US 6,673,010 B2
Jan. 6, 2004

(54) BIOLOGICAL VESSEL SUSPENDING ASSEMBLY AND SYSTEMS AND METHODS UTILIZING SAME

(75) Inventors: Jeff Skiba, Oracle, AZ (US); Ran Oren, Doar Na Oshrat (IL); Dan Moor, Doar Na Oshrat (NL)

(73) Assignee: T. A. G. Medical Products Ltd., Doar Na Oshrat (IL)

( * ) Notice: Subject to any disclaimer, the term of this patent is extended or adjusted under 35 U.S.C. 154(b) by 0 days.

(21) Appl. No.: 09/983,030

(22) Filed: Oct. 22, 2001

(65) Prior Publication Data

US 2003/0078468 A1 Apr. 24, 2003

(51) Int. Cl.[7] .............................. A61F 2/00; A61B 19/00
(52) U.S. Cl. ...................................................... 600/37
(58) Field of Search ........................ 128/885, 897–899, 128/DIG. 25; 600/29–32, 37; 606/139, 148, 151, 185

(56) References Cited

U.S. PATENT DOCUMENTS

| | | | |
|---|---|---|---|
| 5,013,292 A | * | 5/1991 | Lemay ........................ 600/30 |
| 5,019,032 A | * | 5/1991 | Robertson .................... 600/29 |
| 5,041,129 A | | 8/1991 | Hayhurst et al. |
| 5,112,344 A | | 5/1992 | Petros |
| 5,269,809 A | | 12/1993 | Hayhurst et al. |
| 5,518,504 A | * | 5/1996 | Polyak ..................... 623/14.13 |
| 5,562,689 A | * | 10/1996 | Green et al. ................. 606/151 |
| 5,611,515 A | * | 3/1997 | Benderev et al. ............ 128/898 |
| 5,899,909 A | | 5/1999 | Claren et al. |
| 6,042,583 A | * | 3/2000 | Thompson et al. ............ 606/72 |
| 6,077,216 A | * | 6/2000 | Benderev et al. ............. 600/29 |
| 6,110,101 A | * | 8/2000 | Tihon et al. .................. 600/37 |
| 6,117,067 A | * | 9/2000 | Gil-Vernet ................... 600/30 |
| 6,221,005 B1 | * | 4/2001 | Bruckner et al. ............. 600/30 |
| 6,423,080 B1 | * | 7/2002 | Gellman et al. ............. 606/148 |
| 6,478,727 B2 | * | 11/2002 | Scetbon ....................... 600/30 |

* cited by examiner

Primary Examiner—Samuel G. Gilbert
(74) Attorney, Agent, or Firm—G. E. Ehrlich LTD (57) ABSTRACT

A biological vessel suspending assembly is provided. The assembly includes a sling element and at least one anchoring device being attached to at least one end of the sling element, the at least one anchoring device being capable of self anchoring into a tissue to thereby enable suspension of the biological vessel from the sling element, wherein at least a portion of the sling element engaging the biological vessel is configured as a tubular sleeve-like structure capable of rolling upon the biological vessel thus decreasing the likelihood of frictional damage caused by movements of the biological vessel or the sling element at service.

25 Claims, 7 Drawing Sheets

BIOLOGICAL VESSEL SUSPENDING ASSEMBLY AND SYSTEMS AND METHODS UTILIZING SAME

FIELD AND BACKGROUND OF THE INVENTION

The present invention relates to biological vessel suspending assemblies and systems and methods utilizing same, which can be used, for example, in treating urinary incontinence associated with abnormal bladder neck positioning.

Urinary incontinence is characterized by the involuntary loss of urine in individuals. Urinary incontinence affects approximately 13 million people in the United States alone, 85% of them women. Urinary incontinence can be caused by physical stress (stress incontinence) typically brought on by heavy object lifting, coughing, laughing or sneezing, an overactive bladder (typically referred to as urge incontinence) or by an uncontrollable slow leak which is termed flow incontinence, and which is often experienced when complete bladder emptying can not be achieved by an individual. Additional but less common types of urinary incontinence include functional incontinence and unconscious or reflex incontinence.

Of the above causes for urinary incontinence, stress incontinence and urge incontinence are considered the most prevalent. Stress incontinence can be caused by anatomic abnormalities in the positioning of the bladder or bladder neck or by sphincter dysfunction. Urine loss occurs when the intravesical pressure (i.e., the pressure within the urinary bladder) exceeds, even by a small amount, the maximum urethral pressure (i.e., the pressure on the urethra to maintain closure). While the problem of stress incontinence occurs in both men and women, it predominantly occurs in women of childbearing age and beyond.

There are several methods and devices which can be used to alleviate involuntary loss of urine in people suffering from incontinence. Surgery is perhaps the most desirable method in cases of severe incontinence in younger patients. The surgical alternative often involves a procedure whereby the bladder neck is suspended such that the bladder assumes a normal position.

For severe cases of stress incontinence, the surgeon may secure the bladder with a wide sling positioned under the urethra. Such a sling supports the bladder and in addition compresses the bottom of the bladder and the top of the urethra, further preventing leakage.

Abdominal Suspension Procedures

One abdominal suspension procedure is the Marshall Marchetti Krantz (MMK) procedure which is still offered in many medical centers throughout the United States although it is no longer the method of choice.

In the MMK procedure, the bladder neck and urethra are separated from tie back surface of the pubic bone. Sutures are placed on either side of the urethra and bladder neck, which are then elevated to a functional position. The free ends of the sutures are anchored to the surrounding cartilage and pubic bone.

The Burch procedure, also known as Burch colposuspension (vaginal suspension), is often performed in conjunction with an invasive surgical procedure such as abdominal hysterectomy (removal of the uterus). During the suspension procedure, sutures are placed laterally (sideways), this avoiding urethral obstruction and allowing the physician to repair any small cystoceles that may be present. The bladder neck and urethra are separated from the back surface of the pubic bone and the bladder neck is then elevated via lateral sutures that pass through the vagina and Cooper's (pubic) ligaments. The vaginal wall and ligaments are brought together without tension, and the sutures are tied.

Needle Suspension

Needle suspension procedures are simpler to perform and are less invasive than abdominal suspension procedures. Numerous types of transvaginal (through the vagina) needle suspension procedures are known in the art.

In transvaginal needle suspension procedures, sutures are placed blindly through the pubic skin or via a vaginal incision into the anchoring tissues on each side of the bladder neck. The bladder neck is then supported by the sutures, which are tied to the fascia (fibrous tissue) or the pubic bone. Operative times and recovery periods are typically shorter in needle suspension techniques as compared to abdominal suspension procedures.

To enhance tissue anchoring, some needle suspension techniques employ bone anchors such as those provided by the Vesica™ and Intac/Infast™ bladder suspension kits.

Sling Procedures

Patients with severe stress incontinence and intrinsic sphincter deficiency (Type III SUI or weakening of the urethra muscle) may not be treatable via the suspension procedures described hereinabove. Such individuals are good candidates for a pubovaginal sling procedure, which can create the urethral compression necessary to achieve bladder control.

This technique involves the creation of a sling from a strip of tissue taken from the patient's abdominal fascia (fibrous tissue); occasionally, surgeons use a synthetic sling, although urethral erosion appears to be more common when synthetic slings are used.

The strip of fascia is obtained via an incision above the pubic bone. Another incision is made in the front of the vaginal wall, through which the surgeon can grasp the sling and adjust its tension around the bladder neck. The sling is secured in place by sutures which are loosely tied to each other above the incision in the pubic fascia, thus providing a hammock for the bladder neck to rest in.

The pubovaginal sling procedure generally results in high success rates, with bladder control lasting more than 10 years, although complications such as accidental bladder injury, wound infections and prolonged urinary retention severely limit the effectiveness of this technique.

The Vesica™ sling procedure employs two small anchors which are secured into the pubic bone in order to provide stable fixation for a synthetic or natural tissue sling which functions in supporting tie urethra, bladder neck and sphincter.

The Precision Tack™ transvaginal anchor system also employs bone anchors which are secured into the backside of the pubic bone via a minimally invasive procedure. These anchors are connected to a sling via sutures, which sling then functions like a hammock, to support the bladder in a functional position.

Although the above described surgical procedures provide solutions to individuals suffering from urinary incontinence, such procedures suffer from several inherent limitations including the inability to properly tension supporting sutures, which inability results in urethral obstruction thus making self-catheterization or additional surgical intervention necessary.

Limitations of prior art suspension techniques are the major causes underlying a reported 50 to 60% failure rate which is observed therewith following 3 years of service.

In addition, limitations inherent to bladder neck/urethra positioning techniques used by surgeons prior to or during a surgical suspension technique often lead to bladder neck mis-positioning and reduced bladder function.

There is thus a widely recognized need for, and it would be highly advantageous to have, a biological vessel suspending assembly which can be utilized for accurate bladder suspension while being devoid of the above limitations.

SUMMARY OF THE INVENTION

According to one aspect of the present invention, there is provided a biological vessel supporting assembly comprising: a mounting element including at least one anchoring device for anchoring the mounting element within the body cavity; and a sling mountable at its opposite ends to the mounting element and dimensioned to support the biological vessel when the sling is mounted to the mounting element; the sling being adjustably mountable at its opposite ends along the mounting element such as to permit the sling, and the biological vessel when supported thereon, to be precisely positioned within the body cavity.

According to further features in the described preferred embodiments, the sling is of a circular configuration in cross-section such as to produce a low-friction sling contact between the sling and the biological vessel, and thereby to minimize the possibility of damage to the biological vessel when moved with respect to the sling.

According to still further features in the described preferred embodiments, the mounting element includes a flexible suspension strand, and an anchoring device at each of the opposite ends of the suspension strand for mounting the strand in suspension within the body cavity. The sling also includes a flexible strand adjustably mountable at its opposite ends to the flexible suspension strand. Preferably, both the suspension strand and the sling strand are of a flexible, tubular mesh material.

According to still further features in the described preferred embodiments, the sling includes a slider cuff at each of its opposite ends for slidably mounting the opposite ends of the sling to the suspension strand.

According to still further features in the described preferred embodiments, the assembly further comprises an anchor inserter device removably engageable with each of the anchoring devices for inserting the anchoring device into tissue within the body cavity when mounting the suspension strand therein.

According to another aspect of the present invention, there is provided a biological vessel supporting assembly for supporting a biological vessel within a body cavity, comprising: an elongated, flexible suspension strand having an anchoring device at each of its opposite ends for mounting the suspension strand within the body cavity; and a flexible sling strand mountable at its opposite ends to the suspension strand and dimensioned to support the biological vessel; the sling strand, when mounted at its opposite ends to the suspension strand, being movable along the suspension strand such as to permit the sling strand, and the biological vessel when supported thereon, to be precisely positioned within the body cavity.

According to a still another aspect of the present invention, there is provided a method of supporting a biological vessel within a body cavity, comprising: anchoring a mounting element to tissue within the body cavity; mounting a sling to the mounting element; supporting the body cavity on the sling; and moving the sling, and the body cavity supported thereon, along the mounting element to precisely position the biological vessel within the body cavity.

The present invention successfully addresses the shortcomings of the presently known configurations by providing a biological vessel suspending assembly which when utilized for treating urinary incontinence, can be positioned and adjusted through a single trans-vaginal incision rather than the three incisions required for positioning and adjustment of most prior art incontinence systems.

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings:

FIGS. 3a–8b illustrate several configurations of anchoring devices and inserter guide ends; and FIGS. 9a–11 illustrate several configurations of mechanisms used by the assembly of the present invention for adjustment of sling height.

DESCRIPTION OF THE PREFERRED EMBODIMENTS

The present invention is of a biological vessel supporting device and of systems and methods utilizing same. Specifically, the biological vessel suspending assembly of the present invention is designed and configured such that it can be used to accurately and easily suspend a biological vessel using minimally invasive surgical techniques.

The principles and operation of the present invention may be batter understood with reference to the drawings and accompanying descriptions.

Before explaining at least one embodiment of the invention in detail, it is to be understood that the invention is not limited in its application to the details of construction and the arrangement of the components set forth in the following description or illustrated in the drawings. The invention is capable of other embodiments or of being practiced or carried out in various ways. Also, it is to be understood that the phraseology and terminology employed herein is for the purpose of description and should not be regarded as limiting.

One inherent limitation of prior art urethral suspension systems such as the Vesica™ or Precision Tack™ systems described hereinabove, is the high degree of skill required in order to position and adjust such suspension systems within the patient's body. The present invention provides an assembly which integrates tissue anchors with a suspension sling into a configuration which can be positioned and adjusted effortlessly using a minimally invasive procedure while traversing the need for an imaging modality.

Figure 1:
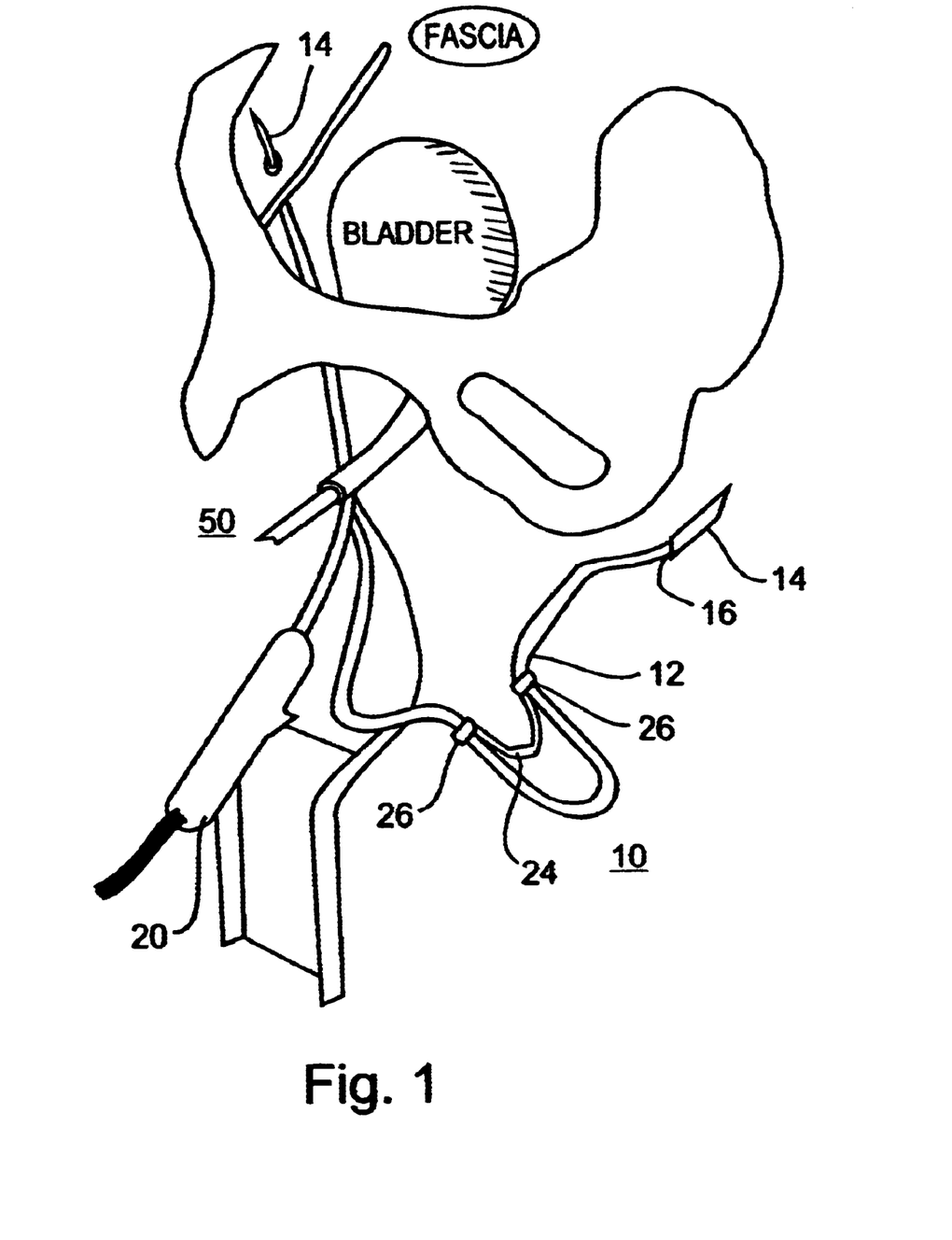
FIG. 1 illustrates the use of an inserter guide for intra-abdominal positioning of the assembly of the present invention.
Figure 2:
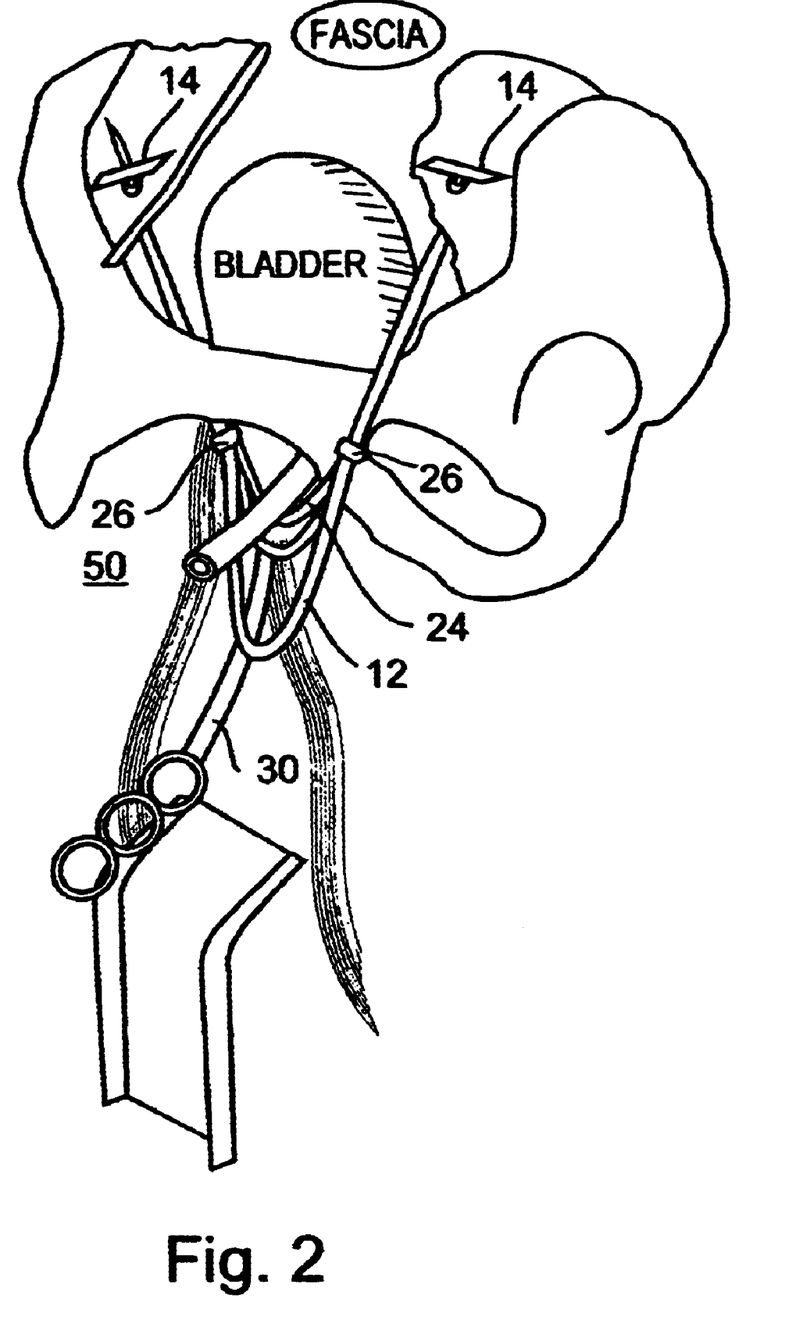
FIG. 2 illustrates the use of an adjuster guide for adjusting the sling height of the assembly of the present invention.

Referring now to the drawings, FIGS. 1 and 2 illustrate a biological vessel suspending assembly which is referred to hereinunder as assembly 10. Assembly 10 of the present invention can be used to suspend any biological vessel including blood vessels, ducts and the like. One preferred use of assembly 10 of the present invention is for the suspension and the correct positioning of the urethra of a descended urinary bladder, which is the major cause of urinary incontinence.

Assembly 10 includes a suspension element 12, at least portion of which is configured as a tubular sleeve-like structure of a mesh pattern, preferably constructed of medical grade woven polymer or any other biocompatible material. As is further detailed hereinbelow, the tubular sleeve-like shape of suspension element 12 provides assembly 10 with several unique and advantageous features. Suspension element 12 slidably mounts a sling element 24, as more particularly described below. Both are preferably made of a strand material. For example, suspension element 12 and sling element 24 shown in FIGS. 1 and 2 may be constructed of two strands which can be interconnected via one of several mechanisms, examples of which are described hereinbelow.

Assembly 10 also includes at least one anchoring device 14 which is constructed of medical grade polymer or any other biocompatible material capable of providing the required anchoring rigidity. In the example illustrated in FIGS. 1 and 2, two anchoring devices 14 are attached to suspension strand 12, each at an end 16 thereof. Anchoring device 14 is designed to be self anchoring into a tissue, preferably, soft tissue, to thereby enable suspension of a biological vessel from suspension strand 12. Anchoring device 14 is constructed such that when deployed, it securely attaches to the tissue, while minimizing tissue damage which can result from force applied on anchoring device 14 by suspension strand 12.

Several configurations of anchoring device 14 are envisaged by the present invention. FIGS. 3a, 4a, 5a, 6a–b, 7a–b and 8a illustrate examples of anchoring device 14. As illustrated by these examples, anchoring device 14 is preferably configured with a piercing element 18 which is designed for insertion of anchoring device into and preferably through tissue such as fascia, muscle and the like.

Figures 5A, 5B:
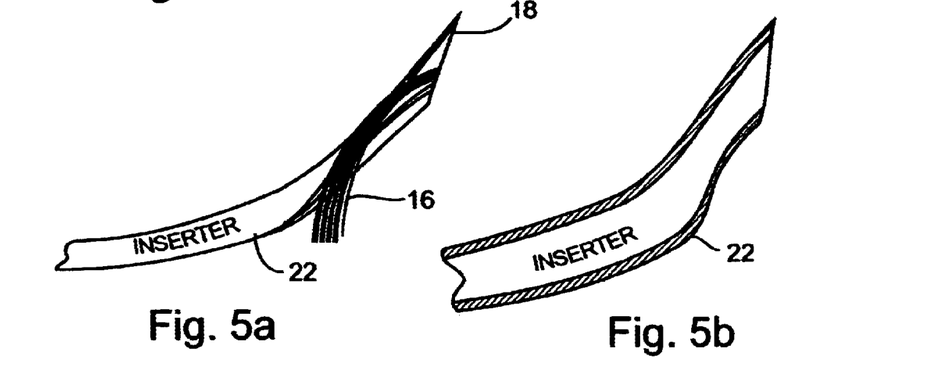

Alternatively, such a piercing element 18 can form a part of an inserter device 20 which is used for inserting anchoring device 14 into the tissue, e.g., as shown in FIGS. 5a and 5b described below.

Figures 3A, 3B:
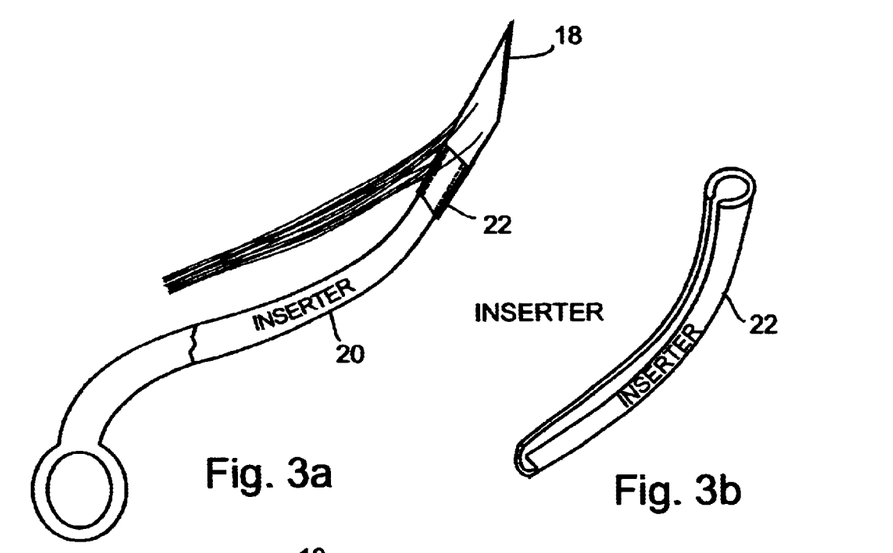

As illustrated in FIG. 3a, such an inserter device 20 is designed to be releasably attached to anchoring device 14. In order to enable such attachment, inserter device 20 is configured with an end portion 22 which is especially adapted for attachment with anchoring device 14. Several attachment configurations are shown in FIGS. 3a–8b. Preferably, end portion 22 of inserter device 20 and anchoring device 14 are designed and configured such that following positioning within a tissue, detachment of inserter device 20 from anchoring device 14 deploys anchoring device 14 within the tissue. For example, the anchoring device can be configured to rotate around the point of attachment to end 16 of sling element 12, such that following insertion of the anchoring device 14 into the tissue, removal of inserter device 20 causes anchoring device 14 to rotate (toggle) 90 degrees into an anchored position (FIG. 2).

Figure 4A:
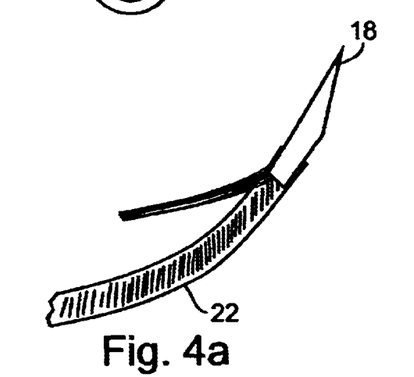
Figure 4B:
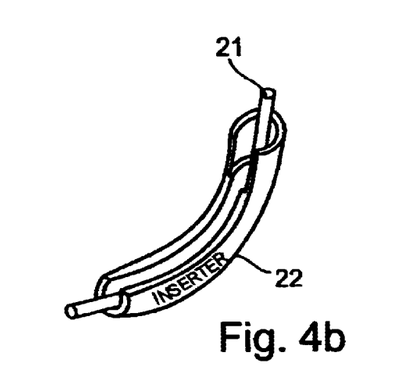
Figure 8A:
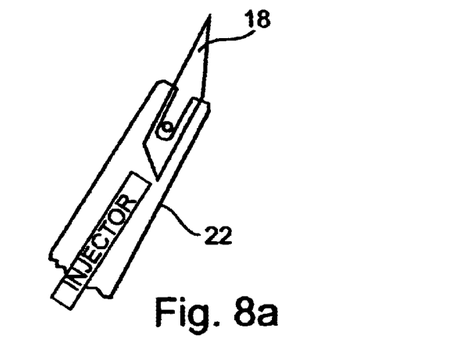
Figure 8B:
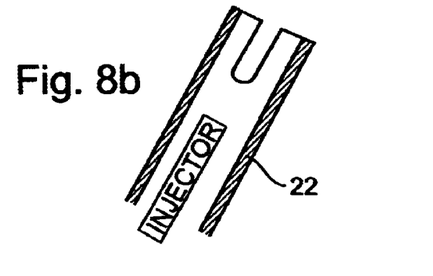
Figures 9A, 9B, 9C:
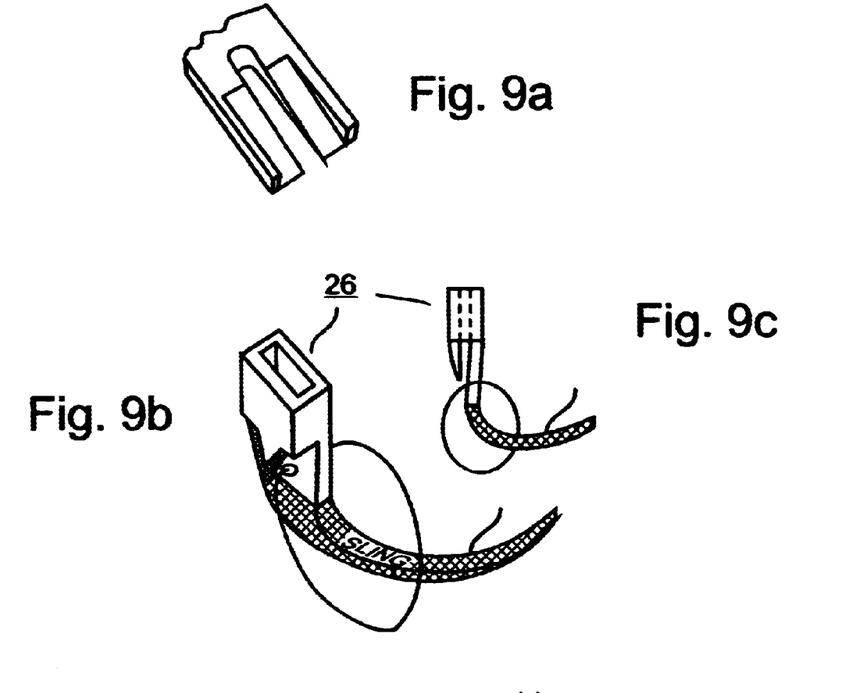
Figure 9D:
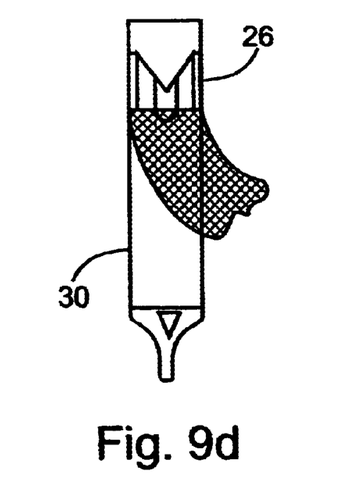
Figure 9E:
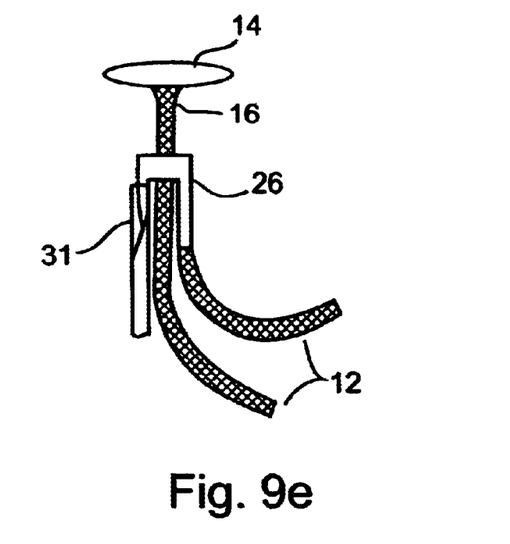

Release of anchoring device 14 from inserter device 20 can be provided by a release mechanism which can be, for example, an ejector rod 21, as shown in FIGS. 4b and 8a, 8b.

Figure 6A:
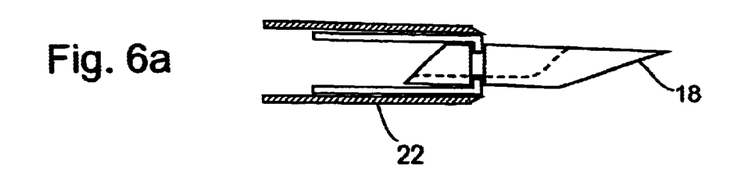
Figures 6B, 7A:
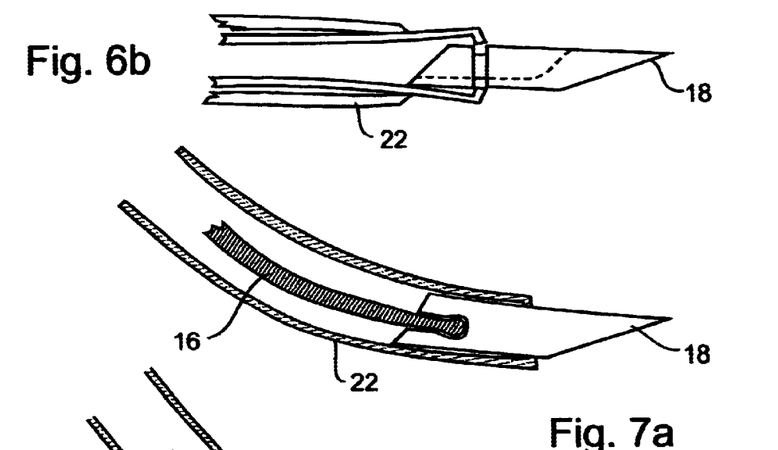
Figure 7B:
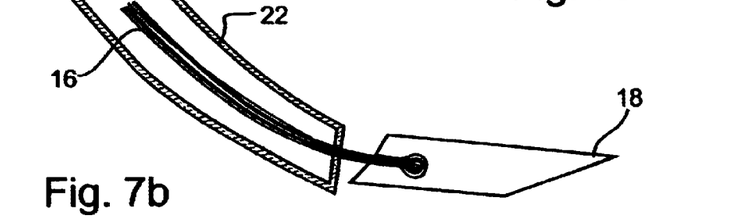

Alternatively, it could be a spring like mechanism, as shown in FIGS. 6a and 6b, which releases anchoring device 14 when inserter device 20 is pulled away from the tissue.

Since assembly 10 of the present invention is designed for suspending and correctly positioning biological vessels, it must be provided with a mechanism permitting accurate adjustment of the distance between a sling strand 24, which engages and supports the biological vessel, and the tissue region in which anchoring device 14 is anchored. Such adjustment would allow correct vessel positioning in individuals exhibiting a wide range of anatomical builds.

FIGS. 1–2 and 9a–11 illustrate several design configurations which enable such distance adjustment.

Assembly 10 can be configured such that distance adjustment is provided by one of several approaches.

Figure 11:
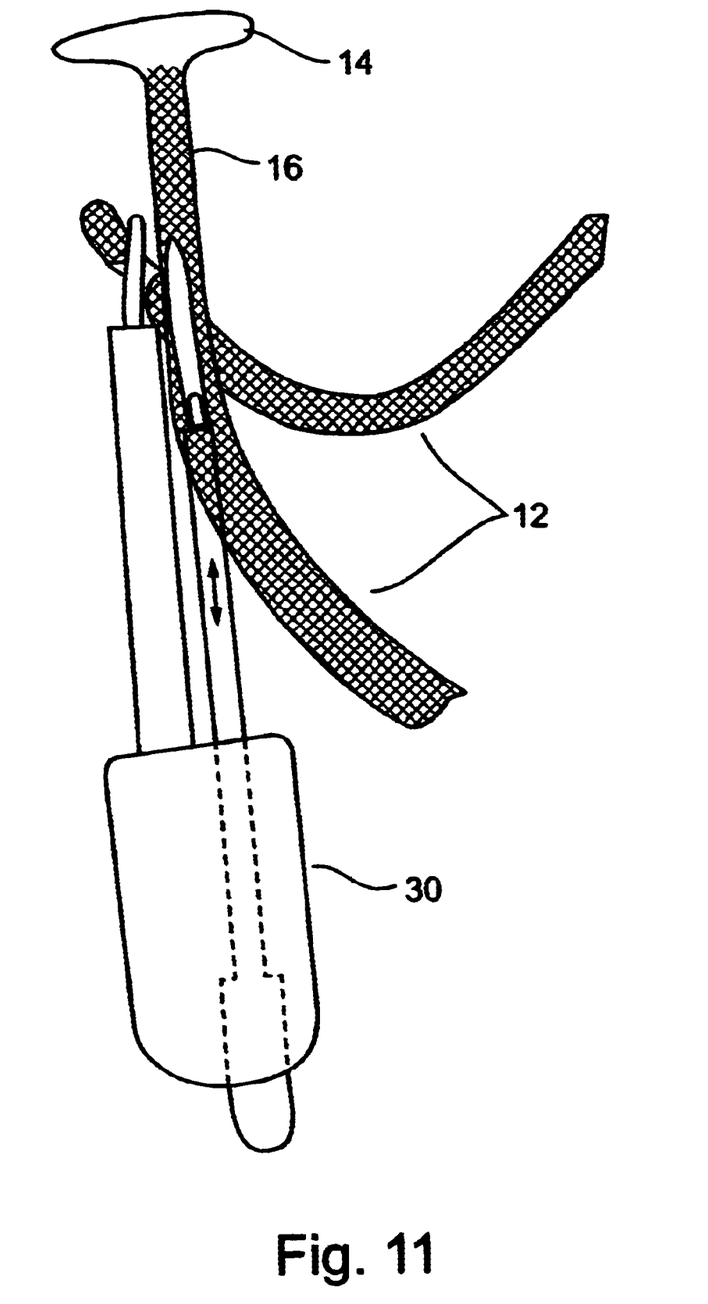

For example, and as illustrated in FIG. 11, distance adjustment can be effected by connecting strands of sling element 12 via a barbed core element; such a barbed core element is designed to be releasable, allowing repositioning if necessary and thus repeated distance adjustments in assembly 10.

Figure 10:
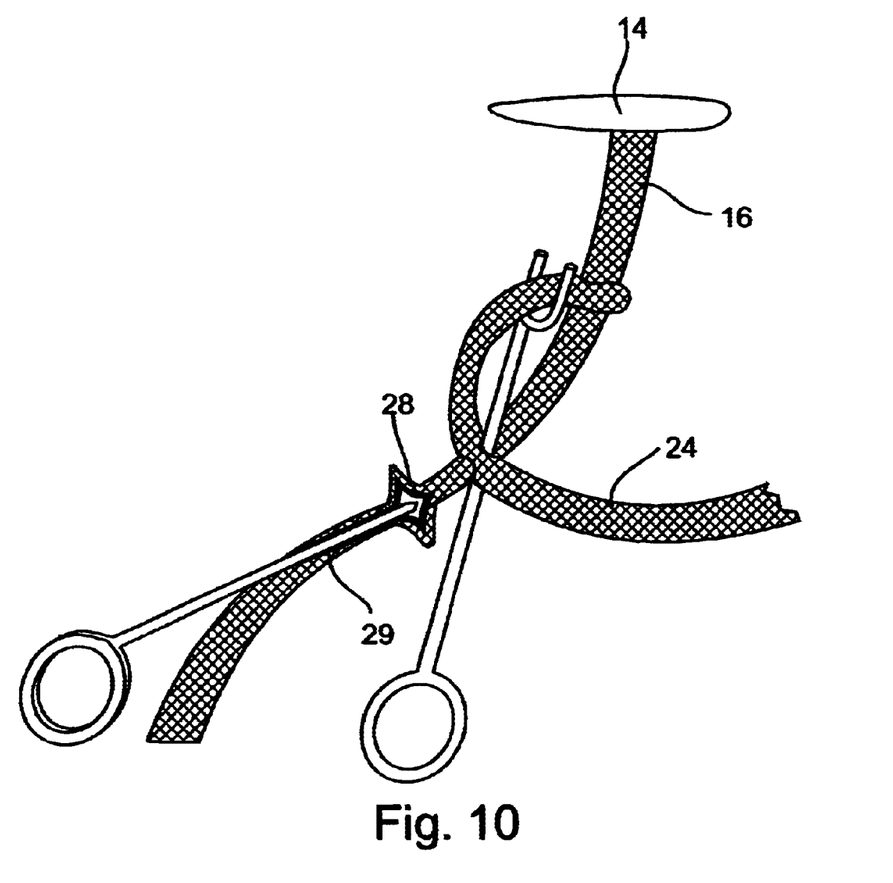

Alternatively, and as shown in FIG. 10, a dedicated device 29 can be used to introduce bulge sites 28 into one strand of sling element 12 which is preferably entirely configured as a tubular mesh. Such bulge sites 28 can be used as stoppages for the strand of region 24.

FIGS. 1 and 2 illustrate a preferred arrangement wherein sling strand 24 includes at each of its ends, a cuff 26 which when moved along suspension strand 24 changes the distance between the sling strand 24 and each anchoring device 14.

As shown in FIGS. 1 and 2, two such cuffs 26 can be used to connect the sling strand 24 with the suspension strand 12 which is connected at its ends to anchoring devices 14.

Movement of cuffs 26, and as such adjustment of the distance between sling strand 24 and anchoring devices 14, can be effected using a dedicated adjuster device 30. Such an adjuster device 30, an example of which is shown in FIG. 2, can be used by a physician to adjust assembly 10 such that the biological vessel supported thereby is correctly positioned.

One preferred configuration of an adjuster guide-cuff mechanism is shown in FIGS. 9a–e. According to this configuration, adjuster guide 30 is provided with an end portion which when engaged with a portion 31 of cuff 26, reduces the frictional pressure of cuff 26 on one strand of sling 12, enabling movement of cuff 26 along that strand and thus distance adjustment.

Such adjustments are particularly important when assembly 10 is used for supporting a urethra of a descended bladder. Whereas accurate positioning of the urethra enables prevention of urinary incontinence problems, inaccurate positioning not only does not prevent accidental voiding of urine, but may also cause additional problems such as, for example, tissue damage or urethral obstruction which oftentimes necessitates catheterization of the patient.

As mentioned above, sling element 24, and also suspension element 12, are preferably formed of a tubular sleeve-like mesh structure. As described below, such a structure provides numerous inherent advantages.

It will be appreciated that during service, some movement of the suspended biological vessel occurs. This movement, which arises from changes in vessel positioning as a result of movement, can lead to frictional damage caused by contact between sling element 24 and the biological vessel.

When sling element 24 of assembly 10 is configured as a tubular sleeve, i.e., of circular configuration in cross-section, it provides: (i) a relatively large area of frictional contact which limits movement, (ii) it rolls upon the biological vessel instead of moving across it, thus substantially decreasing any frictional damage which may result from sling movement, and (iii) tissue growth into the weave of the mesh which progresses with time following implantation of assembly 10, provides a resilient, shock absorbing and friction reducing tissue cushion within the sling 24.

In addition, during service, assembly 10 of the present invention is subjected to considerable pulling forces resultant from movement of a suspended vessel. Thus, the use of a mesh tubular sleeve and integrated deployable tissue anchors provides both a limited degree of wanted compliance and a high degree of resilience against pulling forces which might otherwise dislodge prior art tissue anchors or tear prior art slings.

In sharp contrast, prior art designs which utilize ribbons or strings as slings, do not provide an adequate contact area while producing more frictional damage as a result of sling or vessel movements. In addition, prior art flat ribbon designs, when pulled, tend to re-form into thin rods which can easily damage tissue.

Aside from the advantages described above, assembly 10 of the present invention provides several additional advantages which relate to positioning and deployment thereof.

The integrated anchor-sling configuration of the present invention enables positioning as a single unit, while the design features thereof enable repeated adjustment of suspension, thus enabling a physician to more accurately position assembly 10 within the body and to more accurately and easily adjust assembly 10 in order to achieve an optimal biological vessel position.

FIGS. 1–2 illustrate use of a biological vessel suspending system 50 which includes assembly 10, and inserter guide 20 and/or adjuster guide 30 for treatment of female urinary incontinence.

As illustrated in FIG. 1, an inserter guide 20 which is attached to one or both anchoring devices 14 is inserted into the abdominal cavity through a single trans-vaginal incision (three incisions are typically required for positioning and adjustment of prior art designs). Inserter guide 20 is used to position and anchor anchoring devices 14 within the fascia (rectalis). Following positing of both anchoring devices 14, inserter guide 20 is pulled out and anchoring devices 14 are deployed into an anchoring position.

As illustrated in FIG. 2, an adjuster guide 30, which is inserted through the single trans-vaginal incision used for assembly positioning, is then used to correctly adjust the distance between sling element 24 and each of anchoring devices 14. It will be appreciated that adjuster guide 30 and inserter guide 20 can be incorporated into a single device which can be used for both positioning and distance adjustment.

It will also be appreciated tat since adjustments in assembly 10 can be effected wit ease any number of times, use of the present invention enables far superior positioning accuracy as compared to prior art designs.

A limitation which severely decreases the success rate of prior art surgical suspension techniques is the inability of the surgeon to correctly position the bladder neck and/or the urethra prior to or during a surgical suspension procedure. Since with assembly 10 of the present invention adjustments can be effected at any point in the procedure, and for any number of times, an operating physician can repeatedly test sling positioning until satisfactory results are achieved. For example, the patient can be moved through several positions each time testing the optimal sling-anchor distance until optimal sling height is obtained.

In addition, the simple and integrated design of system 50 of the present invention enables a trained physician to perform procedures, such as the one described above, without the assistance of an imaging modality.

In addition to the above described application, system 50 and in particular assembly 10 can be utilized for various other applications.

As a body ages and experiences the effects of gravity, tissue compliance is altered leading to changes in tissue strength and as such support. In some cases this change in tissue compliance is cosmetic, while in others it alters normal physiological function.

Thus, restoration of tissue positioning and support is another object of the present invention. For example, the present invention can be utilized in various tissue lift procedures as well as for correcting vaginal prolapse, cystoceles, practical, and the like.

It is appreciated that certain features of the invention, which are, for clarity, described in the context of separate embodiments, may also be provided in combination in a single embodiment. Conversely, various features of the invention which are, for brevity, described in the context of a single embodiment, may also be provided separately or in any suitable subcombination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

What is claimed is:

1. A biological vessel supporting assembly for supporting a biological vessel within a body cavity, comprising:

a mounting element for anchoring said mounting element within the body cavity, said mounting element including a flexible suspension strand and an anchoring device at each of the opposite ends of the suspension strand for mounting said strand in suspension within said body cavity;

and a sling mountable at its opposite ends to said mounting element and dimensioned to support said biological vessel when the sling is mounted to said mounting element;

said sling being slidably mountable at its opposite ends to said suspension strand such as to permit the sling, and the biological vessel when supported thereon, to be precisely positioned within said body cavity.

2. The assembly according to claim 1, wherein said sling is of a circular configuration in cross-section such as to produce a low-friction rolling contact between the sling and the biological vessel, and thereby to minimize the possibility of damage to the biological vessel when moved with respect to the sling.

3. The assembly according to claim 1, wherein said sling includes a flexible sling strand slidably mountable at its opposite ends to said flexible suspension strand.

4. The assembly according to claim 3, wherein said suspension strand and said sling strand are both of a flexible, tubular mesh material.

5. The assembly according to claim 1, wherein said sling includes a slider cuff at each of its opposite ends for slidably mounting said opposite ends of the sling to said suspension strand.

6. The assembly according to claim 1, wherein each of said anchoring devices is coupled at an intermediate portion thereof to its respective end of the suspension strand to permit the anchoring device, after piercing tissue within the body cavity when mounting the suspension strand therein, to rotate to a locking position with respect to said tissue.

7. The assembly according to claim 6, wherein each of said anchoring devices has a pointed tip for piercing tissue within the body cavity when mounting the suspension strand therein.

8. The assembly according to claim 1, wherein said assembly further comprises an anchor inserter device removably engageable with each of said anchoring devices for inserting the anchoring device into tissue within the body cavity when mounting said suspension strand therein.

9. The assembly according to claim 8, wherein said inserter device has a pointed tip for piercing tissue within the body cavity when mounting said suspension strand therein.

10. The assembly according to claim 8, wherein said inserter device includes an ejector for ejecting therefrom the anchoring device after inserted into said tissue.

11. The assembly according to claim 8, wherein the end of said inserter device engageable with the anchoring device includes a pair of spring arms which lock the anchoring device to the inserter device during the insertion of the anchoring device into the tissue, and thereafter release the anchoring device from the inserter device after insertion of the anchoring device into the tissue.

12. The assembly according to claim 1, wherein said assembly further comprises a sling adjuster device removable engageable with the opposite ends of said sling for moving the sling with respect to said suspension strand to precisely position the sling, and the biological vessel thereon, within said body cavity.

13. A biological vessel supporting assembly for supporting a biological vessel within a body cavity, comprising:

an elongated, flexible suspension strand having an anchoring device at each of its opposite ends for mounting the suspension strand within the body cavity;

and a flexible sling strand mountable at its opposite ends to said suspension strand and dimensioned to support said biological vessel;

said sling strand, when mounted at its opposite ends to said suspension strand, being movable along said suspension strand such as to permit the sling strand, and the biological vessel when supported thereon, to be precisely positioned within said body cavity.

14. The assembly according to claim 13, wherein said sling strand is of a circular configuration in cross-section such as to produce a low-friction rolling contact between the sling strand and the biological vessel, and thereby to minimize the possibility of damage to the biological vessel when moved with respect to the sling strand.

15. The assembly according to claim 13, wherein the opposite ends of said sling strand carry cuffs slidable along said suspension strand.

16. The assembly according to claim 13, wherein each of said anchoring devices is coupled at an intermediate portion thereof to its respective end of the suspension strand to permit the anchoring device, after being passed through tissue within the body cavity when mounting the suspension strand therein, to rotate to a locking position with respect to said tissue.

17. The assembly according to claim 16, wherein each of said anchoring devices has a pointed tip for piercing tissue within the body cavity when mounting the suspension strand therein.

18. The assembly according to claim 13, wherein said assembly further comprises an anchor inserter device removably engageable with each of said anchoring devices for inserting the anchoring device into tissue within the body cavity when mounting said suspension strand therein.

19. The assembly according to claim 18, wherein said inserter device has a pointed tip for piercing tissue within the body cavity when mounting said suspension strand therein.

20. The assembly according to claim 13, wherein said inserter device includes an ejector for ejecting therefrom the anchoring device after inserted through said tissue.

21. The assembly according to claim 20, wherein the end of said inserter device engageable with the anchoring device includes a pair of spring arms which lock the anchoring device to the inserter device and release the anchoring device from the inserter device after insertion of the anchoring device into the tissue.

22. The assembly according to claim 13, wherein said assembly further comprises a sling adjuster device removable engageable with the opposite ends of said sling strand for moving the sling strand with respect to said suspension strand to precisely position the sling strand, and the biological vessel thereon, within said body cavity.

23. A method of supporting a biological vessel within a body cavity, comprising:

mounting a mounting element in suspension from tissue within the body cavity by anchoring the opposite ends of said mounting element to said tissue;

suspending a sling from said mounting element;

supporting the biological vessel on said sling;

and sliding said sling, and the biological vessel supported thereon, along said mounting element to precisely position said biological vessel within said body cavity.

24. The method according to claim 23, wherein said sling is in the form of a flexible strand and is dimensioned to support said biological vessel.

25. The method according to claim 23, wherein said sling is slidably mounted at its opposite ends to said mounting element by means of cuffs fixed to said sling and slidable with respect to said mounting element.

* * * * *